United States Patent [19]
Cozean et al.

[11] Patent Number: 5,707,368
[45] Date of Patent: Jan. 13, 1998

[54] CONTACT TIP FOR LASER SURGERY

[75] Inventors: Colette Cozean, El Toro; Robert J. Freiberg, Mission Viejo, both of Calif.

[73] Assignee: Premier Laser Systems, Inc., Irvine, Calif.

[21] Appl. No.: 457,992

[22] Filed: Jun. 1, 1995

Related U.S. Application Data

[63] Continuation of Ser. No. 291,344, Aug. 16, 1994, abandoned, which is a continuation of Ser. No. 150,276, Nov. 10, 1993, abandoned, which is a continuation of Ser. No. 999,572, Dec. 30, 1992, abandoned, which is a continuation of Ser. No. 643,570, Jan. 18, 1991, abandoned, which is a continuation-in-part of Ser. No. 607,372, Oct. 31, 1990, abandoned.

[51] Int. Cl.$^6$ .................................................. A61N 5/06
[52] U.S. Cl. ............................ 606/15; 606/17; 606/27
[58] Field of Search .............................. 606/2, 3–18, 27, 606/28

[56] References Cited

U.S. PATENT DOCUMENTS

| | | |
|---|---|---|
| 2,247,258 | 6/1941 | Shepard . |
| 3,467,098 | 9/1969 | Ayres . |
| 3,865,113 | 2/1975 | Sharon et al. . |
| 3,865,114 | 2/1975 | Sharon . |
| 4,126,136 | 11/1978 | Auth et al. . |
| 4,185,633 | 1/1980 | Prozorov et al. . |
| 4,209,017 | 6/1980 | Shaw .................................. 606/10 |
| 4,233,493 | 11/1980 | Nath . |
| 4,273,127 | 6/1981 | Auth et al. . |
| 4,449,528 | 5/1984 | Auth et al. . |
| 4,539,987 | 9/1985 | Nath et al. . |

(List continued on next page.)

FOREIGN PATENT DOCUMENTS

| | | |
|---|---|---|
| 9100062 | 1/1991 | European Pat. Off. ................. 606/16 |
| 2303516 | 8/1976 | France . |
| 2717423 | 4/1977 | Germany . |
| 2826383 | 12/1979 | Germany . |
| 258360A1 | 7/1988 | Germany . |
| 2185565 | 5/1987 | United Kingdom .................... 606/13 |
| WO89/03202 | 4/1989 | WIPO . |

OTHER PUBLICATIONS

A. Sagi et al., "Heating and cutting of biological tissue by highly absorbed laser beams: theoretical model and experiments", SPIE vol. 1201 Laser-Tissue Interaction (1990) pp. 228–233.

S. Ashley et al., "Thermal and optical behaviour of sapphire fibertips for laser angioplasty", SPIE vol. 1201, Optical Fibers in Medicine V (1990) pp. 137–144.

R. Steiner et al., "Comparison of core fibers and contact probes for laser surgery", SPIE vol. 1201 Optical fibers in Medicine V (1990) pp. 277–283.

RM Verdaasdonk et al., "Optically modified fiber tips penetrate tissue only when 'dirty'", SPIE vol. 1201 Optical Fibers in Medicine V (1990), pp. 129–136.

*Primary Examiner*—David M. Shay
*Attorney, Agent, or Firm*—Knobbe, Martens, Olson & Bear, LLP

[57] ABSTRACT

A laser surgery apparatus including a contact tip comprising an input face having a surface for receiving laser energy from an optical waveguide directed along an axis of propagation. The surface is inclined relative to the axis of propagation such that an angle of incidence between the laser light and the surface is approximately equal to Brewster's angle. Another aspect of the invention includes coating a portion of the tip body with a coating that is reflective to the laser energy. One preferred embodiment comprises a tip body coated with a single coating consisting essentially of a material which is biologically compatible with tissue to prevent generation of a toxic tissue response. A further aspect of the invention includes a tip configuration having a generally conical exterior with a substantially flat surface disposed obliquely to a core axis of the tip body. An additional feature on the invention includes a shield to protect tissue adjacent to the shield from undesired thermal damage by preventing the transfer of thermal energy through the shield.

31 Claims, 7 Drawing Sheets

U.S. PATENT DOCUMENTS

| | | | |
|---|---|---|---|
| 4,542,987 | 9/1985 | Hirschfeld | 374/131 |
| 4,592,353 | 6/1986 | Daikuzono | 606/16 |
| 4,627,435 | 12/1986 | Hoskin | 606/16 |
| 4,648,892 | 3/1987 | Kittrell et al. | 606/7 |
| 4,672,961 | 6/1987 | Davies . | |
| 4,693,244 | 9/1987 | Daikuzono | 606/16 |
| 4,693,556 | 9/1987 | McCaughan, Jr. | 606/16 |
| 4,736,743 | 4/1988 | Daikuzono | 606/16 |
| 4,760,845 | 8/1988 | Kovalcheck | 606/28 |
| 4,832,979 | 5/1989 | Hoshino | 606/15 |
| 4,848,339 | 7/1989 | Rink et al. | 606/16 |
| 4,878,492 | 11/1989 | Sinofsky et al. | 606/13 |
| 4,994,060 | 2/1991 | Rink et al. | 606/16 |
| 5,246,436 | 9/1993 | Rowe . | |

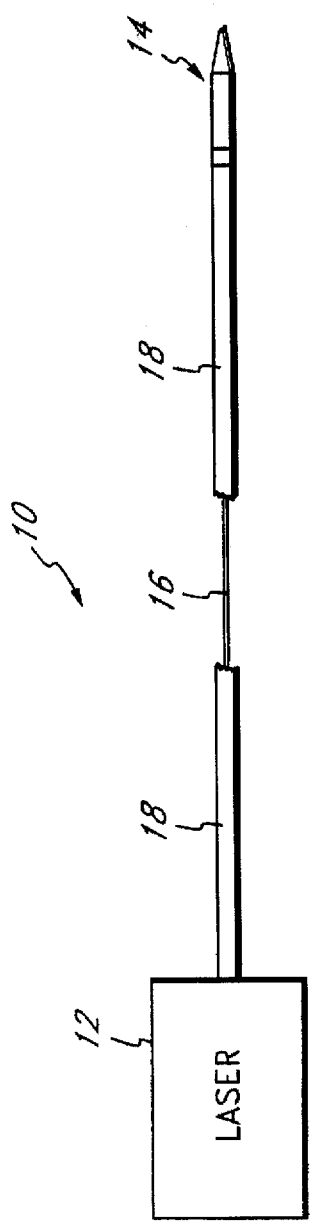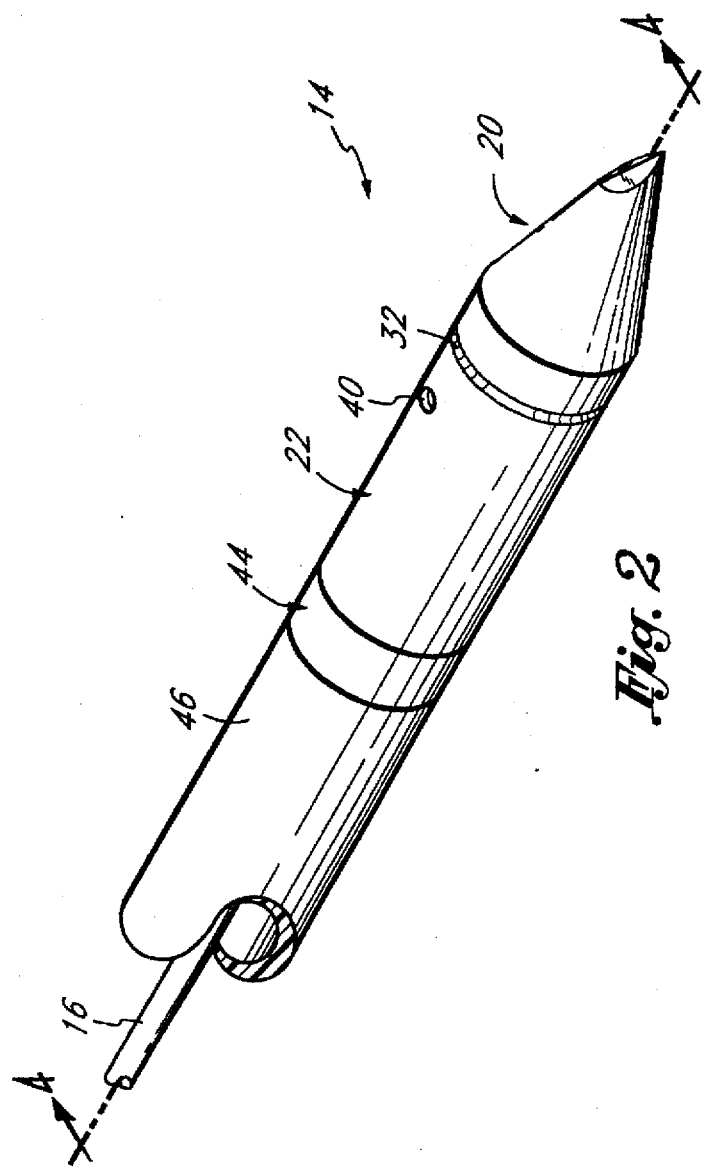

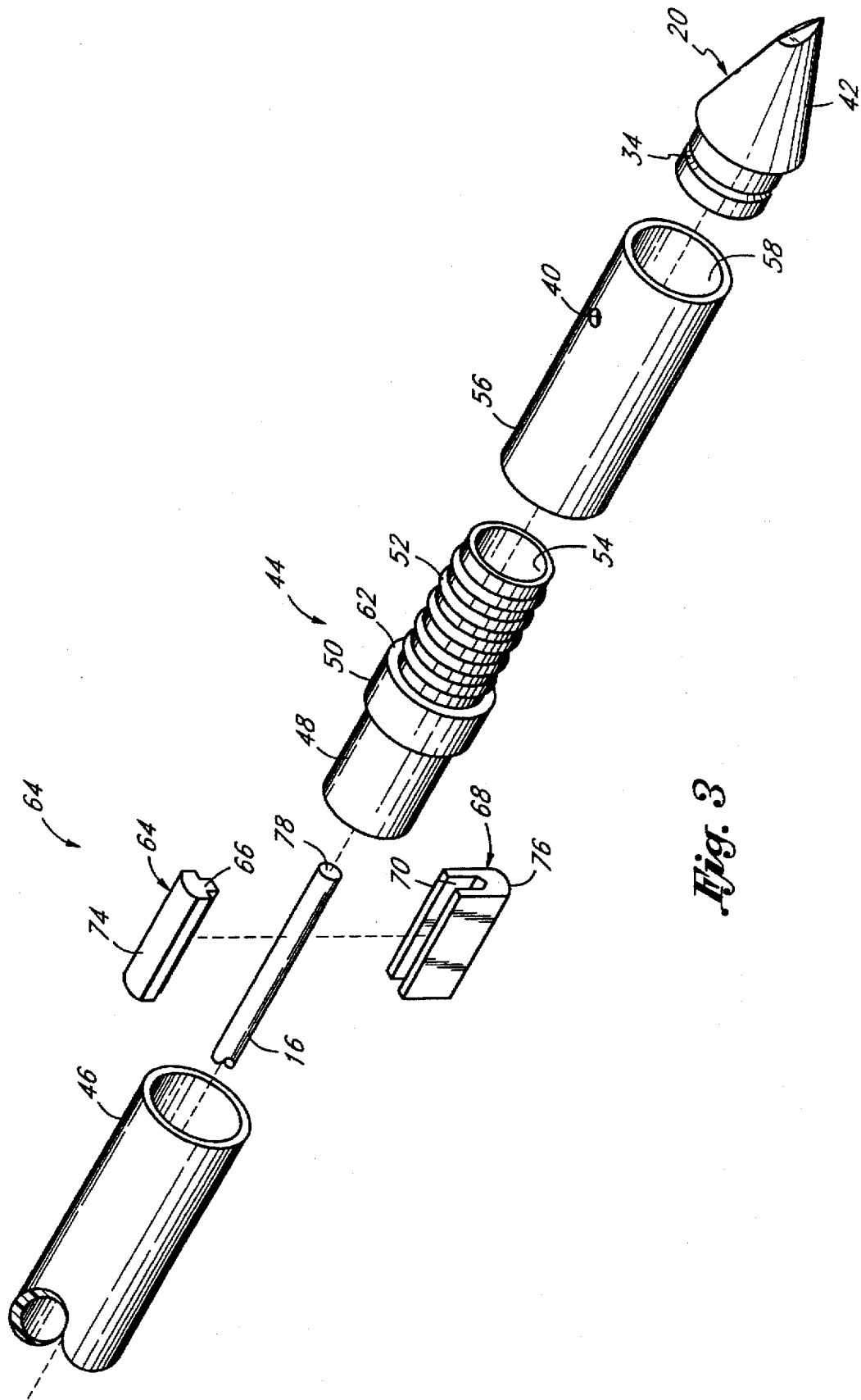

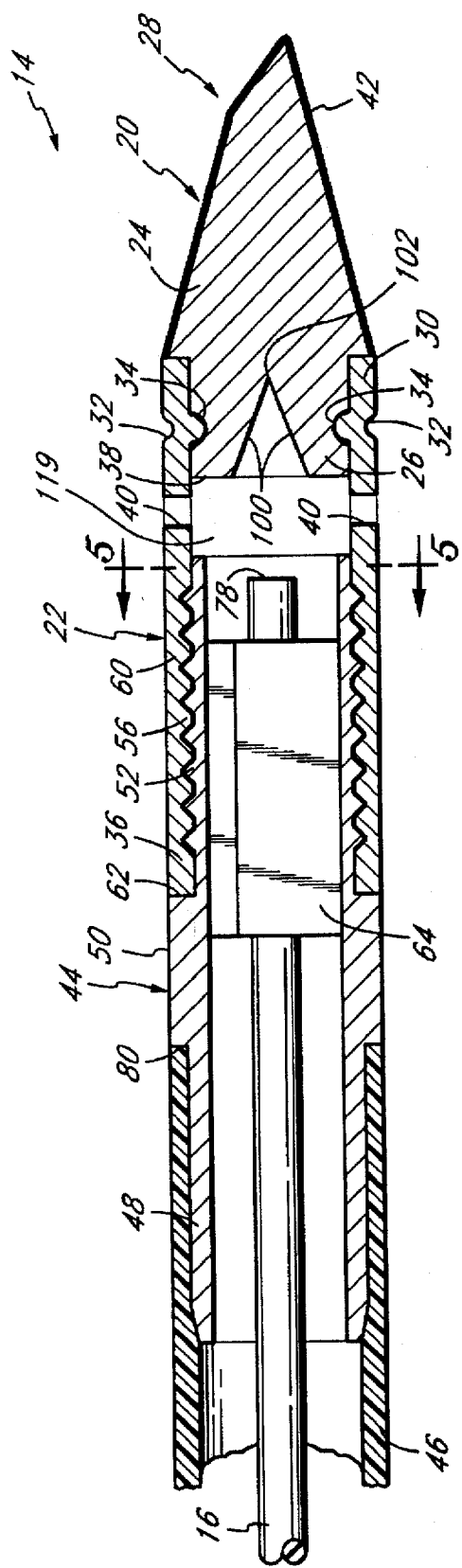
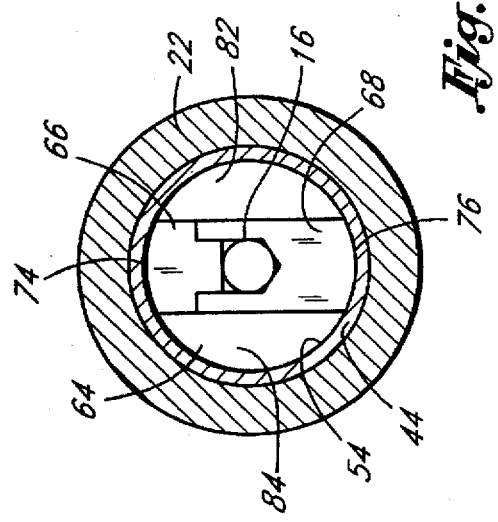
Fig. 4
Fig. 5

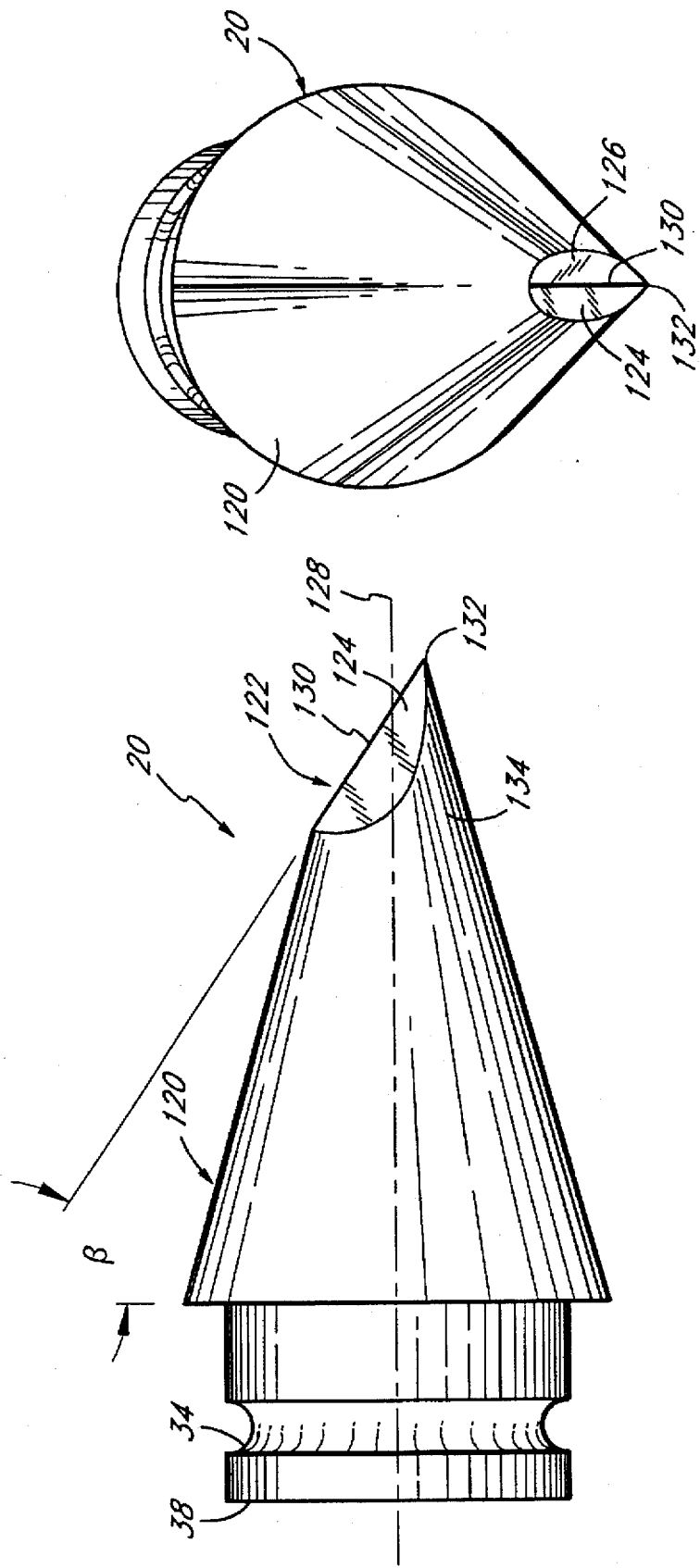

CONTACT TIP FOR LASER SURGERY

This application is a continuation of application Ser. No. 08/291,344, filed Aug. 16, 1994, which is a continuation application of Ser. No. 08/150,276, filed Nov. 10, 1993, which is a continuation application of Ser. No. 07/999,572, filed Dec. 30, 1992, which is a continuation Ser. No. 07/643,570, filed Jan. 18, 1991, which is a continuation-in-part application, Ser. No. 07/607,372, filed Oct. 31, 1990 (all now abandoned).

The present invention relates generally to laser surgery probes, and particularly to probes having contact tips which are heated by laser energy.

Contact tips are commonly used in laser surgery for a variety of procedures, including surgical incisions and coagulation. Typically, such contact tips comprise a tip body of a transparent material such as sapphire which is capable of withstanding high temperatures. The sapphire may be coated with a coating that is absorptive to laser energy. Absorption of the laser energy heats the tip to high temperatures suitable for tissue vaporization. One problem with such tips, however, is that they do not distribute the laser energy evenly and thus heating is not uniform. Further, due to toxicity or other adverse effects of the coating, an overcoat of, for example, ceramic or glass, must be applied to prevent the coating from contacting the tissue. Examples of contact tips utilizing absorptive coatings are disclosed in U.S. Pat. Nos. 4,736,743 and 4,832,979.

Typically, contact tips receive laser energy from a waveguide, such as an optical fiber. Laser light propagates out of the waveguide end through an air gap and strikes an input face of the contact tip. The input face is generally normal to the axis of propagation. Because the indices of refraction between the waveguide, the air gap and the contact tip material do not match, some radiation is reflected from the input face, resulting in build up of thermal energy.

When operating with laser surgery contact probes, surgeons use a variety of tip shapes, depending on the type of incision or degree of coagulation required. Typically, contact tips configurations are conical, hemispherical, flat or chisel-shaped, and a complete set of tips can be expensive. Moreover, the inconvenience of changing a tip and the time involved in doing so is a disadvantage to tactile laser surgery.

Surgeons further have difficulty in using contact tips in confined areas, particularly in tight endoscopic environments. Because of the confined surgical site, inadvertent contact with healthy tissue often occurs resulting in undesired thermal damage.

SUMMARY OF THE INVENTION

The laser surgery apparatus of the present invention comprises a contact tip having a tip body. An input face of the tip body receives laser energy from an optical waveguide. The tip body is coated with a coating that is reflective to the laser energy. Such reflectivity causes the laser energy to be distributed substantially evenly throughout the tip to provide generally uniform heating.

In a preferred embodiment, the tip body comprises a substantially transparent material, and the coating forms a reflective cavity around the substantially transparent material. The coating consists essentially of a single coating material, such as tantalum, which is biologically compatible, and the transparent material comprises a crystalline material such as $Al_2O_3$ (i.e., sapphire).

In an alternative preferred embodiment, the laser surgery apparatus comprises a contact tip which receives laser energy. The tip comprises a tip body coated with a coating consisting essentially of a material which is biologically compatible with tissue to prevent generation of a toxic tissue response. Due to the biological compatibility, overcoating the coating material is unnecessary. In the preferred embodiment, the coating material comprises an elemental metal, such as tantalum, and the tip body comprises $Al_2O_3$ (i.e., sapphire). Such coating forms a surface which is reflective for wavelengths over the entire optical spectrum.

In accordance with another aspect of the invention, the laser surgery apparatus comprises a contact tip including an input face having a surface for receiving laser light propagating along an axis of propagation defined by an optical waveguide. The surface of the input face is inclined relative to the axis of propagation such that an angle of incidence between the laser light and the surface is approximately equal to Brewster's angle. In this manner, essentially all of parallel polarized light transmits to the tip with the perpendicular polarized light reflecting off the surface. In a preferred embodiment, the surface is a smooth, conical shape extending into the body of the contact tip, which comprises $Al_2O_3$ (i.e., sapphire). Longitudinally, the surface is generally linear. As a result of the conical shape, the initially reflected light will strike the surface multiple times until the bulk of the remaining energy is transmitted to the contact tip.

In accordance with a third aspect of the invention, the laser surgery apparatus comprises a contact tip which receives laser light. The tip comprises a tip body having a generally conical exterior with a substantially flat surface disposed obliquely to a cone axis of the tip body. In a preferred embodiment, the tip body further comprises an obliquely truncated tip and a second substantially flat surface disposed obliquely to the first flat surface. The first and second flat surfaces intersect proximal to the truncated tip to form an edge extending from the truncated tip across the truncated surface.

In accordance with a fourth aspect of the invention, the laser surgery apparatus comprises a contact tip which receives laser light and a shield. The tip absorbs at least a portion of the laser energy, thus heating the tip. The shield, being thermally shielded from hot tip, protects the tissue adjacent to the shield from undesired thermal damage by preventing the transfer of thermal energy through the shield. In a preferred embodiment, the contact tip may have an offset conical shape. In other preferred embodiments, the contact tip may have a generally wedge shape or a generally hemispherical shape. Preferably, the shield extends circumferentially around the contact tip throughat least 30° of circumference and extends longitudinally along a major portion of the contact tip. In accordance with an alternative preferred embodiment, the shield has a generally semi-circular shape in the axial direction and extends longitudinally beyond the contact tip end. Additionally, the surgery apparatus includes at least one and preferably a plurality of cooling gas channels disposed around the contact tip base directing a flow of gas between the shield and the hot tip to thermally shield the shield for the hot contact tip.

BRIEF DESCRIPTION OF THE DRAWINGS

FIG. 1 is a schematic illustration of the laser surgery apparatus of the present invention showing the laser, the optical fiber, the catheter and the laser probe;

FIG. 2 is a perspective view of the laser probe according to one preferred embodiment of the present invention;

FIG. 3 is an exploded perspective view of the laser probe of FIG. 2;

FIG. 4 is a cross-sectional view of the laser probe of FIG. 2 taken along line 4—4;

FIG. 5 is a cross-sectional view of the laser probe of FIG. 4 taken along line 5—5;

FIG. 7 is a side plan view of the laser probe contact tip of FIG. 4;

FIG. 8 is a perspective frontal view of the laser probe contact tip of FIG. 7;

DETAILED DESCRIPTION OF THE PREFERRED EMBODIMENT

Figure 6:
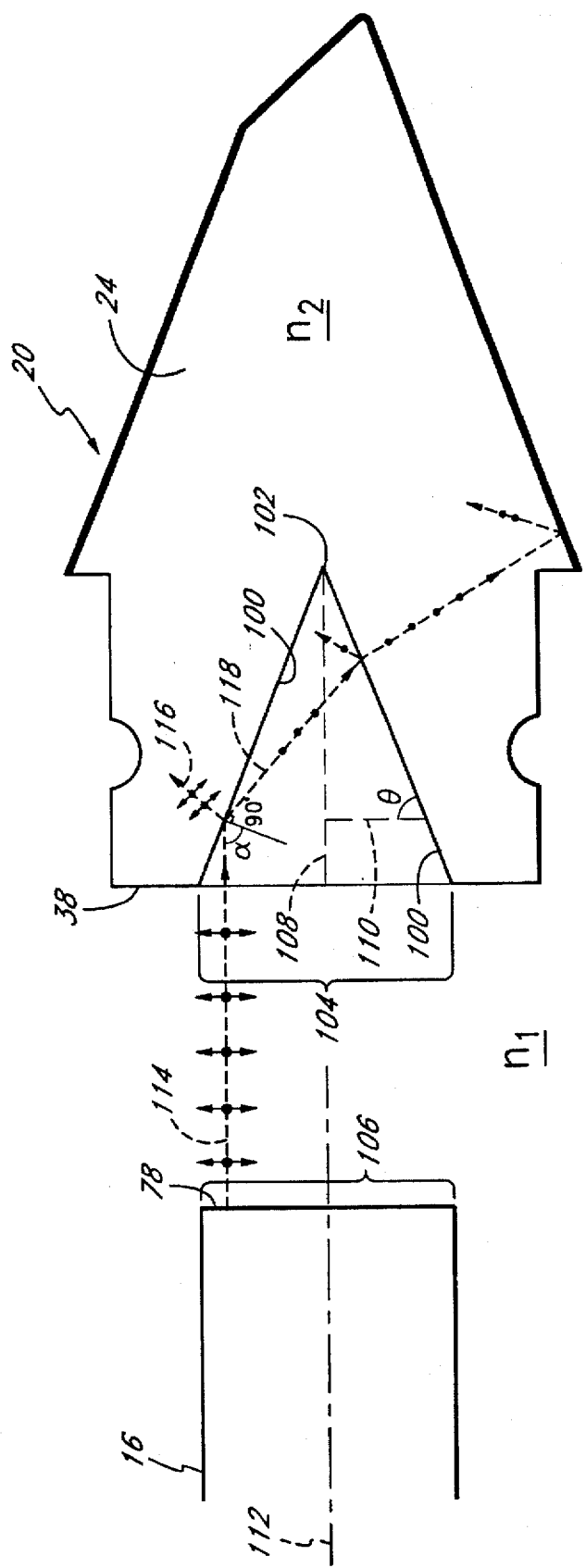
FIG. 6 is a schematic illustration showing laser light propagation transmission and reflection in relation to the laser probe contact tip of FIG. 4.

As shown in FIG. 1, the laser surgery apparatus 10 of the present invention comprises a laser 12 which supplies laser energy to a laser probe 14. Light from the laser 12 is coupled to a waveguide, such as an optical fiber 16, that guides the laser energy to the probe 14. The optical fiber 16 is surrounded by a catheter 18 which extends from the laser 12 to the probe 14. The catheter 18 may, for example, be connected to a source of cooling fluid, such as gas, in a conventional manner. Such cooling fluid is conducted along the catheter 18 from the laser 12 to the probe 14 in order to cool the fiber 16 and the probe 14.

Referring to FIG. 2, the distal end of probe 14 comprises a tip mount 22 comprising a tubular metal sleeve which mounts a contact tip 20. As used herein, the words proximal and distal are used in reference to proximity to the laser 12 which supplies the light to the fiber 16. Although the contact tip 20 in FIG. 2 is shown as being generally conically tapered with a truncated tip, it will be understood that other tip configurations, such as hemispherical, flat, chisel-shaped, etc., may be used alternatively. As shown in FIG. 4, the contact tip 20 includes a body portion 24 having a proximal end 26 and a distal end 28. The proximal end 26 is mounted in a distal end 30 of the tubular tip mount 22 by forming a crimp 32 in the tip mount distal end 30. The proximal end 26 of the contact tip body 24 includes a circumferential groove 34 which receives the axially compressed material of the crimp 32. The tip body 24 is comprised of a material which can withstand temperatures on the order of 500° C. or more, and a preferred material is crystalline Al$_2$O$_3$ (i.e., sapphire). Diametrically opposed exit ports 40 are provided in the tip mount sleeve 22 adjacent to the tip input face 38 to permit the cooling fluid flowing through the catheter 18 (FIG. 1) to escape.

Referring to FIGS. 2, 3, 4 and 5, the proximal end of probe 14 comprises a fiber holder sleeve 44, the proximal end 36 of the tip mount sleeve 22, a fiber holder 64 (FIGS. 3 and 5) and a distal end 46 of the catheter 18 (FIGS. 2 and 3); each component preferably comprises a durable, heat-resistant and corrosion-resistant material. A brass alloy, half-hard, is contemplated for use in the structural components 44, 22, 64, and 18, in combination with an outer protective plating comprising gold 15 millionths of an inch thick followed by a nickel strike 5 millionths of an inch thick.

The fiber holder sleeve 44 comprises a proximal sleeve portion 48, a central sleeve portion 50, and distal sleeve portion 52, as shown in FIG. 4. The fiber holder sleeve 44 is cylindrical and has an axial bore 54 (FIGS. 3 and 5) of uniform diameter throughout its length. The distal portion 52 of the fiber sleeve 44 has a reduced wall thickness relative to the central portion 50 so as to provide a reduced outside diameter. Threads 56 are disposed on the exterior surface of distal portion 52.

The tip mount sleeve 22 has a uniform diameter bore 58 (FIGS. 3 and 5) throughout its length. As shown in FIG. 4, the proximal end portion 36 of the tip mount sleeve 22 is tapped with female threads 60 for mating with the male threads 56 on the distal sleeve portion 52 of the fiber holder sleeve 44. The tip mount sleeve 22 is secured to the fiber holder sleeve 44 by screwing the male threads 56 of the fiber holder sleeve 44 into the female threads 60 until the proximal end portion 36 of the tip mount sleeve 22 abuts a shoulder 62 on the central portion 50 of the fiber holder sleeve 44. A water-tight seal between the tip mount sleeve 22 and fiber holder sleeve 44 can be provided by the use of an appropriate washer, gasket or sealant compound, in the art. The outside diameters of the tip mount sleeve 22 and the central sleeve portion 50 of the fiber holder sleeve 44 are identical at their interface so as to avoid exterior surface irregularities in the laser probe 14.

Referring to FIG. 3, the fiber holder 64 comprises an elongate member 66 having a T-shaped cross section and an elongate member 68 having a U-shaped cross section. The member 66 has a channel 70 with a width approximately equal to that of the optical fiber 16. As shown in FIG. 3, the members 66, 68 are configured such that a central leg 72 of the T-shaped top member 66 fits snugly into the channel 70 formed in the U-shaped bottom member 68. The length of the central leg 72 is less than the depth of the channel 70 by an amount equal to the diameter of the optical fiber 16, so as to provide an elongate opening in which the optical fiber 16 is disposed. The optical fiber 16 is retained between the members 66, 68 by an interference fit or, alternatively, by chemical adhesive.

As shown in FIGS. 3 and 5, the fiber holder 64 has opposing top and bottom surfaces 74, 76 on the members 66, 68, respectively, which have a curvature corresponding to the curvature of the axial bore 54 of the fiber holder sleeve 44. The members 66, 68 of the fiber holder 64 are sized for insertion into the bore 54 of the sleeve 44, such that the distance between the curved outer surfaces 74, 76 is approximately equal to the diameter of the bore 54, thereby permitting the fiber holder 64 to fit snugly in the sleeve 44. Preferably, the fiber holder is affixed to the sleeve 44 by a chemical adhesive. As shown in FIG. 5, the width of the fiber holder 64 is significantly less than the diameter of the bore 54 to provide side channels 82, 84 for the passage of fluid around the fiber holder 64. The fiber holder 64 retains the fiber 16 in an axial orientation such that the fiber axis is aligned with the central axis of the sleeves 44, 22. Preferably, the distal end 78 of the fiber 16 protrudes only a very small amount past the fiber holder to prevent sagging or bending of the end 78. The orientation of the fiber holder 64 within the fiber holder sleeve 44 is such that the optical fiber 16 placed therein is centered and axially aligned with the contact tip 20. The fiber 16 is held stationary within the fiber holder sleeve 44 so that the distance between the contact tip 20 and the distal end 78 of the fiber 16 remains constant. However, the relative position of the fiber end 78 and contact tip 20 can be adjusted by repositioning the fiber holder 64 within the fiber holder sleeve 44.

The optical fiber 16 is a multi-mode fiber comprising a core of relatively high refractive index which is surrounded by a cladding of relatively low refractive index. The core can be made of pure silica which has been fused, and the cladding which surrounds the core may comprise fused silica which has been doped to lower the refractive index. The core material is preferably significantly free of metallic impurities, resulting in less attenuation of the transmitted laser energy as it travels through the fiber 16. Specific purpose fibers, which are readily available and known in the art, may be desirable for certain wavelengths which are difficult to transmit through optical fibers. For example, UV grade fibers may be appropriate for very short wavelengths and zirconium fluoride fibers have been found to be advantageous for long wavelengths. Further, hollow core waveguides have found application in some cases.

The length of the fiber 16 is typically about 50 to 500 cm, and preferably about 200 to 400 cm. In one embodiment, the core has a diameter 106 (FIG. 6) of approximately 600 microns. Fiber core diameters for medical applications are typically in the range from 200 to 600 microns.

The optical fiber 16 is surrounded by a protective catheter sleeve 18 comprised of materials, such as PVC, cured epoxy or Teflon. The catheter sleeve 18 has an outside diameter which is equal to that of the central portion 50 of the fiber holder sleeve 44. In the preferred embodiment, the catheter diameter is 2.2 mm. In general, the diameter of the catheter sleeve 18 will typically be no more than 4.0 mm. The proximal portion 48 of the fiber holder sleeve 44 has an outside diameter which is reduced relative to the central portion 50 by twice the thickness of the catheter sleeve 18 to allow the catheter sleeve 18 to snugly fit over the portion 48, with the distal end of the catheter sleeve 46 abutting a shoulder 80 (FIG. 4) on the central portion 56 of the fiber holder sleeve 44. This permits the outer surface of the catheter sleeve 18 to blend smoothly into the outer surface of the probe assembly 14 without surface irregularities. Preferably, the catheter sleeve 18 is affixed to the portion 48 by chemical adhesive to insure a water-tight connection.

The portion of the tip body 24 that extends from the tip mount sleeve 22 is coated with a coating 42. In the preferred embodiment, the coating comprises a broadband reflective material, such as a metal, which is reflective for wavelengths over the entire optical spectrum. While a variety of coating materials may be utilized, and the coating may include an undercoat or overcoat, the coating of the preferred embodiment comprises a single coating material having a substantially uniform composition. Preferably, the coating material is selected to provide good adherence to the tip body 24 so as to prevent flaking or other deleterious effects. In addition, the coating material (and oxides thereof) is preferably a biologically compatible material that will not generate a toxic tissue response or other biological incompatibility when used in a laser surgery environment. Examples of biologically compatible materials which can be applied directly to $Al_2O_3$ (without undercoat) include tantalum, tungsten, titanium, and vanadium. Although all of these coating materials have good adherence properties for a tip body comprised of $Al_2O_3$ and exhibit good biological compatibility without the need for an overcoat, tantalum is presently considered to be the preferred material, due to its excellent adherence properties and biological compatibility. Gold may also be a suitable material for some applications, however, it has been found that gold does not adhere as well to $Al_2O_3$ as the above-mentioned materials unless an undercoat, e.g., of nickel, is utilized.

Prior to coating, a sapphire blank is machined to produce the desired tip configuration. The resulting exterior surface finish is smooth but unpolished (i.e., not optical quality). After forming the contact tip body 24, a metallization source is used to deposit a metal coating 42 over the portion of the contact tip 20 which extends from the tip mount sleeve 22. The metal coating 42 is evaporated onto the structure using conventional metal evaporation processes. The resulting coating 42 is a thin metal film over a portion of the exterior of the contact tip body 24. Although the coating 42 is hard, the coating 42 does not structurally support itself. Instead, the structure of the tip body portion 24 maintains the shape of the contact tip 20.

In use, the coated portion of the contact tip 20 is applied directly to tissue to form, e.g., a surgical incision or to coagulate the tissue. The reflective coating 42 forms a reflective cavity for the laser energy, and multiple reflections within this cavity distribute the laser energy substantially evenly throughout the cavity, thereby providing substantially uniform heating of the coating 42 along the entire length of the tip. Such reflection also serves to prevent significant amounts of laser energy from escaping the tip, and thus permits the tip 20 to be heated to high temperatures with relatively low input energy. Moreover, because the coating 42 is biologically compatible, it can be applied directly to the tissue without a protective overcoat.

Contact tips coated in this manner can be used with a variety of laser sources, including Erbium YAG, Neodymium YAG, Argon and $CO_2$. Advantageously, these coated tips add a thermal characteristic to laser sources which previously lacked cauterizing ability, i.e., Erbium YAG, Neodymium YAG and Argon lasers.

Referring to FIGS. 4 and 6, the input face 38 has a smooth generally conical surface 100 which extends from the periphery of the input face 38, into the contact tip body 24 and to a vertex 102. Longitudinally, the surface 100 is linear. The conical surface 100 defines a recess in the contact tip body having a diameter 104 at the input face 38 that is substantially equal to or greater than the optical fiber core diameter 106. As shown in FIG. 6, the surface 100 is inclined from a line 108 bisecting the vertex 102 such that an angle θ, formed between the surface 100 and a line 110 perpendicular to the bisecting line 108, is substantially equal to Brewster's angle. As known in the art, Brewster's angle is equal to $\tan^{-1} n_2/n_1$, where $n_1$ equals the refractive index of the cooling fluid (gas in the preferred embodiment) and $n_2$ equals the refractive index of the contact tip body material, as shown in FIG. 6.

In assembly, the bisecting line 108 is substantially parallel to an axis of propagation 112 and preferably coincides with the axis of propagation 112. In this manner, as schematically shown in FIG. 6, an angle of incidence α between the laser light 114 and the conical surface 100 is approximately equal to Brewster's angle. As a result, essentially all of the parallel polarized laser light 116 is transmitted to the contact tip body 24 and the perpendicular polarized laser light 118 is reflected. The initially reflected light 118, however, strikes an opposing side of the conical surface 100 at a decreased angle of incidence, and thereby transmits a substantial portion of the reflected light into the tip body 24. The remaining incident laser light will undergo multiple reflections along the conical surface 100 until substantially all of laser light is transmitted to the contact tip body 24. As a result of the conical shape and of the initial angle of incidence being equal to Brewster's angle, less radiation is reflected, thereby reducing the amount of thermal energy build up.

As shown in FIG. 4, the distal end 78 of the optical fiber 16 is disposed proximal to the conical surface 100 with a small gap 119 formed between the components 78, 100. Although the laser light 114 may diverge somewhat while propagating through the gap 119 filled with cooling fluid, essentially all of the light will strike the conical surface 100 at an angle of incidence α approximately equal to Brewster's angle because of the narrowness of the gap 119.

Referring to FIGS. 7 and 8, the contact tip 20 preferably includes a generally conical portion 120 having a truncated tip portion 122 defining an apex 132. The truncated tip portion 120 also includes a pair of substantially flat surfaces 124, 126 disposed obliquely to a cone axis 128 of the conical portion 120 and proximal to the apex 132. The flat surfaces 124, 126 intersect each other and form an edge 130 extending from the apex 132.

This contact tip configuration is accomplished by truncating a tip of a cone at an angle β with respect to the base of the cone, as shown in FIG. 7. Using a secondary machining operation, two substantially flat, intersecting surfaces 124, 126 are cut on the cone to form a cutting edge 130 along a line starting from the apex 132 of the truncated tip 122 and extending along a line of symmetry of the truncated surface.

Although the preferred embodiment of the tip 20 has the coating 42 over the entire exposed surface thereof, the coating may be alternatively applied only to selected portions of the tip 20. For example, the coating 42 may be applied only to the conical portion 120 and may be omitted from the surfaces 124, 126 of the truncated tip portion 122 such that light is transmitted from the tip 20 through the surfaces 124, 126 to irradiate the tissue.

When used in surgical operations, the contact tip 20 offers the surgeon a variety of working surfaces enabling various types of incisions and degrees of coagulation with one contact tip. Cutting similar to a conventional conical tip is achieved by placing the apex 132 of the truncated tip 122 in contact with the tissue. Scalpel like cutting comparable to that achieved with a conventional chisel tip is accomplished by drawing the sharp edge 130 across the tissue. Tissue coagulation is achieved by placing the large curved surface 134 or the flat surfaces 124, 126 in contact with the tissue. The curved surface 134 and the flat surfaces 124, 126 simulate conventional hemispherical and flat shaped contact tips, respectively.

While the preferred embodiment of the contact tip configuration is shown and described above as a truncated conical tip, it will be understood that other configurations are possible to provide multi-functional surfaces in a single tip. For example, contact tip 20a can have a generally conical exterior with a substantially flat surface disposed obliquely to the axis of the conical tip. The contact tip 20a can further have a second flat surface intersecting the first flat surface to produce a sharp edge. Additionally, these flat surfaces can be positioned with respect to an apex of the tip such that the edge extends from the apex, as is the case in the preferred embodiment.

Figure 9:
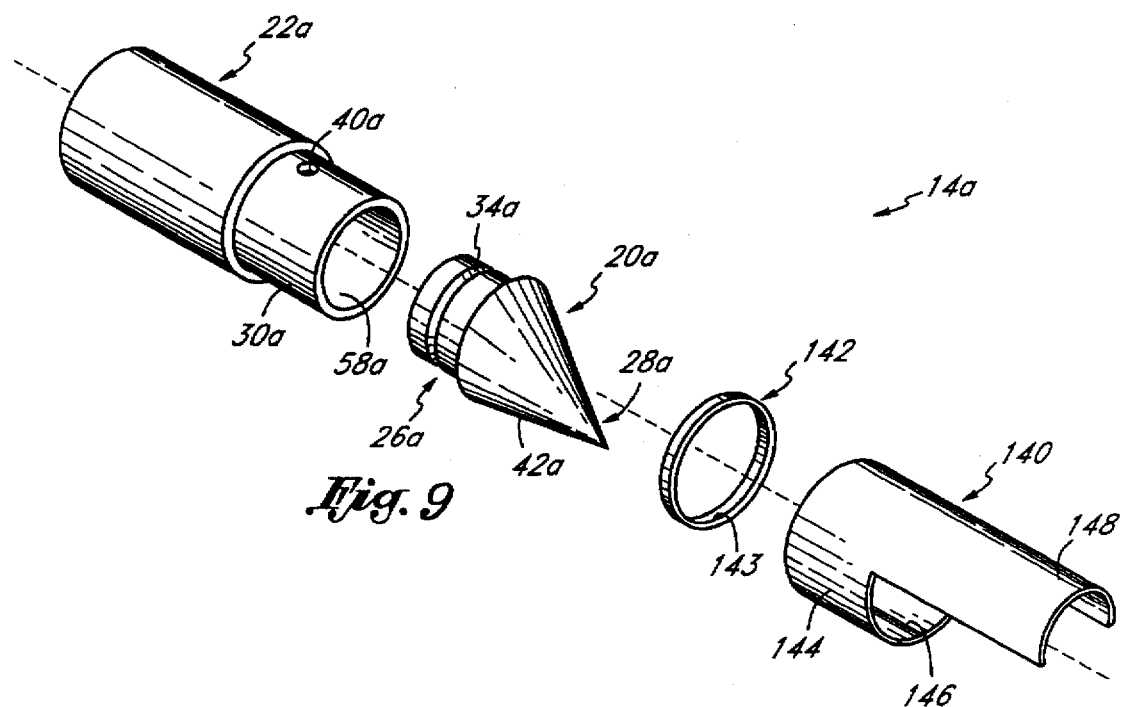
FIG. 9 is an exploded perspective view of another preferred embodiment of a laser probe including a shield.
Figure 10:
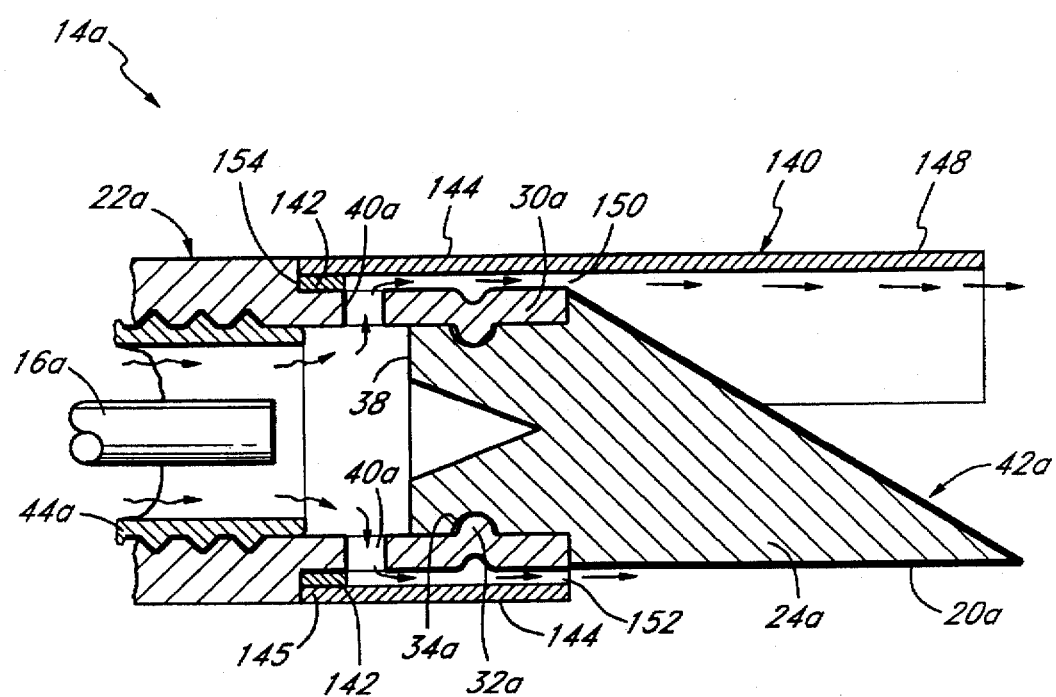
FIG. 10 is a cross-sectional assembly view of the laser probe of FIG. 9.

In an alternative preferred embodiment, as shown in FIGS. 9 and 10, the probe assembly 14a includes a shield 140 which is thermally shielded from the hot contact tip 20a. Where appropriate, like numbers with an "a" suffix have been used to indicate like parts of the two embodiments for ease of understanding. The shield 140 protects the tissue adjacent to the shield from undesired thermal damage by preventing the transfer of thermal energy through the shield 140.

Referring to FIG. 9, the distal end of the probe 14a comprises a tip mount sleeve 22a, a contact tip 20a, a thermal insulation pad 142, and a shield 148. The proximal end of the probe 14a is identical to that previously describe above. Although the contact tip in FIG. 9 is shown being generally conical, it will be understood that other tip configurations, such as hemispherical, flat, chisel-shaped, etc., may be used alternatively. As shown in FIG. 9, the contact tip 20a includes a body portion 24a having a proximal end 26a and a distal end 28a. The proximal end 26a is mounted in a distal end 30a of the tubular tip mount 22a by forming a crimp 32a in the tip mount distal end 30a. The proximal end 26a of the contact tip 20a includes a circumferential groove 34a which receives the axially compressed material of the crimp 32a. The tip body 24a is comprised of a material which can withstand temperatures on the order of 500° C. or more, and a preferred material is crystalline $Al_2O_3$ (i.e., sapphire).

As shown in FIG. 9, the distal portion 30a of the tip mount sleeve 22a has a reduced wall thickness so as to provide a reduced outer diameter. The tip mount sleeve 22a further includes a pair of diametrically opposed exit ports 40a adjacent to the input face 38a to permit the cooling fluid flowing through the catheter 18 (FIG. 1) to escape. Although the preferred embodiment employs two exit ports, it will be understood that there must be at least one exit port 40a and can be a plurality of exit ports spaced axially about the circumference of the tip mount sleeve 22a.

The thermal insulation pad 142 has a generally circular shape with an inner diameter 143 sized larger than the outer diameter of the distal end portion 30a. The thermal insulation pad comprises thermal insulation material, as known in the art, and is thick enough to provide thermal shielding of the shield 140 from the contact tip 20a. In other words, a large percentage of the heat collected in the contact tip 20a is not transmitted to the shield 140 because of the thermal insulation pad 142.

Figure 12:
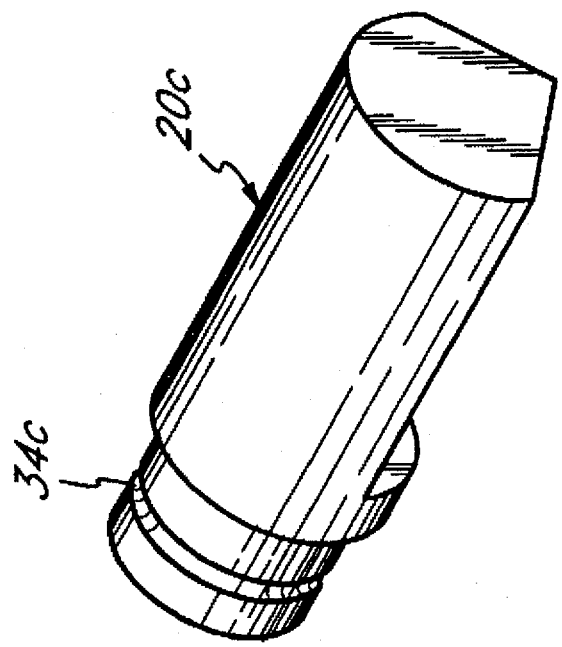
FIG. 12 is a perspective view showing a wedge-shaped contact tip.

Preferably, the configuration of the contact tip 20a used with the shield 140 is diametrically asymmetric with respect to the axial center-line of the probe 14a such that at least one radius, of a cross section taken along the distal end 28a of the contact tip 20a, is of greater length than its opposing radius (i.e., the radius in the 180° direction). Examples of diametrically asymmetric shapes are an offset conical (as shown in FIGS. 9 and 10) and a wedge shape (as shown in FIG. 12). In assembly with the shield 140, the diametrically asymmetric shaped contact tip 20a is preferably disposed such that a portion of the contact tip 20a is opposite a portion of the shield 140 and extends longitudinally in a direction generally parallel to a portion of the shield 140. In this manner, the functional surfaces of the contact tip 20a (e.g., the apex and rounded surfaces of the offset conical) are accessible to contact tissue while the opposite, non-functional surfaces of the contact tip 20a are shielded from the tissue by shield 140.

Figure 11:
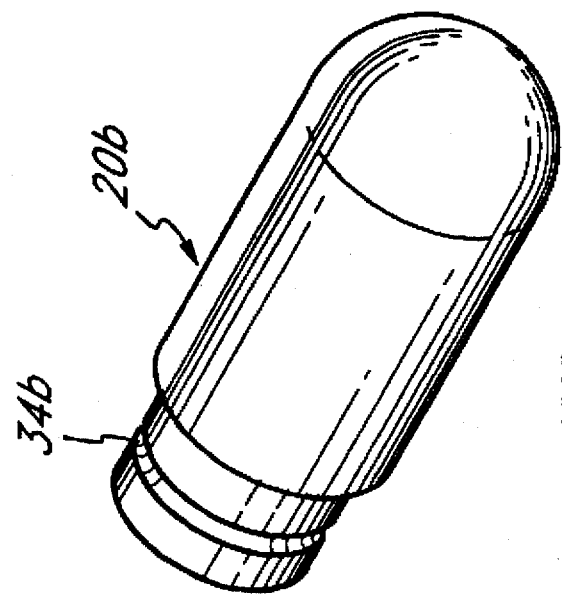
FIG. 11 is a perspective view showing a hemispherical contact tip.

The shield 140 comprises a proximal portion 144 having an inner diameter 146 and a distal portion 148. The inner diameter 146 of the shield proximal portion 144 is larger than the outer diameter of the thermal insulation pad 142. The distal portion 148 extends circumferentially around the contact tip 20a through at least 30° of circumference and preferably through 180° of circumference (i.e., the distal portion 148 has a semi-circular cross-sectional shape). As shown in FIG. 10, the contact tip 20a preferably has a generally offset conical tip and the shield 148 preferably extends longitudinally along a major portion of the contact tip 20a. In other words, the shield distal end portion 148 terminates near the contact tip distal end 28a. In other preferred embodiments, the distal portion 148 can extend slightly beyond the distal end 28a of the contact tip 20a, especially when used with a contact tip having a hemispherical or wedge-shape configuration, as shown in FIGS. 11 and 12, respectively.

In assembly, as shown in FIG. 10, the thermal insulation pad 142 slides over the tip mount sleeve distal end 30a to a position abutting shoulder 154. The shield 140 is coupled to the tip mount sleeve 22a by inserting the tip mount sleeve distal end 30a into the shield proximal end 144 to a position where the shoulder 154 abuts the proximal end 144 of the shield 140. The outside diameters of the tip mount sleeve 22a and the shield 140 are identical at their interface so as to avoid exterior surface irregularities in the laser probe 14a. The shield 140 is secured to the tip mount sleeve 22a by spot welding the two components together, as known in the art. The spot welds (not shown) are positioned along the circumference of the shield proximal end 144 on the proximal side of the exit ports 40a. Assembled in this manner, channels 150, 152 are formed between the tip mount sleeve distal end 30a and the shield proximal end 144 and direct the flow of cooling fluid exiting ports 40a over the shield 140 and the contact tip 20a. The flow of gas through and out of the channel 150 thermally shields the shield 140 from the heat radiating off of the hot contact tip 140. In other words, a large percentage of the heat radiating off the contact tip 20a is transmitted to the cooling fluid by convection and is dissipated by the cooling fluid flow. As a result, the shield 140 maintains a temperature much cooler than the temperature of the contact tip 20a.

What is claimed is:

1. A laser surgery apparatus, comprising:
   a contact tip comprising a tip body having an input face comprising a surface for receiving laser light from an optical waveguide along an axis of propagation, said surface being inclined relative to the axis of propagation such that an angle of incidence between the laser light and the surface is substantially equal to Brewster's angle, whereby light polarized parallel to the surface is substantially entirely transmitted through said surface without reflection.

2. The apparatus of claim 1, wherein said surface is a smooth conical shape extending into said contact tip body.

3. The apparatus of claim 2, wherein said surface is linear and forms a vertex located within said contact tip body.

4. The apparatus of claim 3, wherein said vertex is disposed on said axis of propagation.

5. The of claim 1, wherein said tip body comprises substantially transparent material.

6. The apparatus of claim 5, wherein said substantially transparent material comprises crystalline material.

7. The apparatus of claim 6, wherein said crystalline material comprises $Al_2O_3$.

8. A laser surgery apparatus, comprising:
   a surgical tip for tactile interaction with tissue comprising a tip body, said tip body comprising a curved surface which is conically tapered and a first substantially flat surface disposed relative to said curved surface such that said curved and flat surfaces intersect along a line extending proximal to an apex of said tip body, wherein said tip body further comprises a second substantially flat surface disposed relative to said first flat surface such that a wedge is formed along a line of intersection between said first and second flat surfaces.

9. The apparatus of claim 8, wherein said wedge and said first and second flat surfaces are proximal to said apex.

10. The apparatus of claim 8, wherein said wedge extends to said apex.

11. The apparatus in claim 8, wherein said tip body further comprises an obliquely truncated tip.

12. The apparatus of claim 11, wherein said edge extends from said truncated tip.

13. The apparatus of claim 11, wherein said curved surface is proximal to said truncated tip.

14. A laser surgery apparatus, comprising:
   a contact tip comprising an input face for receiving laser energy from an optical wave guide, a portion of said contact tip being configured for contact with tissue, and being coated with a coating that is reflective to said laser energy, the tissue contacting portion of said contact tip comprising a curved surface which is conically tapered and a first substantially flat surface disposed relative to said conically tapered surface such that said curved surface and flat surface intersect along a line extending proximal to an apex of said contact tip, wherein said contact tip further comprises a second substantially flat surface disposed relative to said first flat surface, said first and second flat surfaces intersecting to form a wedge.

15. The apparatus of claim 14, wherein said input face comprises a surface for receiving laser light along an axis of propagation, said surface being inclined relative to the axis of propagation such that an angle of incidence between said laser light and said surface is substantially equal to Brewster's angle, whereby light polarized parallel to said surface is substantially entirely transmitted through the surface, without reflection.

16. The apparatus of claim 14, wherein at least one of said substantially flat surface is not coated with said coating such that said laser energy is transmitted through said flat surface for irradiation of tissue.

17. The apparatus of claim 14, wherein said tip body comprises a substantially transparent material, said coating forming a reflective cavity around said substantially transparent material.

18. The apparatus of claim 16, wherein said coating consists essentially of a single coating comprising at least one biologically compatible material selected from the group consisting of tantalum, vanadium, titanium and tungsten.

19. A laser surgery apparatus, comprising:
   a laser which produces optical energy having a wavelength;
   an optical waveguide with a contact tip at an end thereof, said waveguide connected to receive said energy from said laser and deliver said energy to an interior of said contact tip such that substantially the entire interior of said contact tip receives said optical energy from said waveguide, said contact tip having a tissue contacting portion for contact with tissue, said contact tip comprised of a substantially optically transparent substrate, substantially all of the optical energy passing through said contact tip contacting an exterior surface of said transparent substrate, said contact tip additionally comprising a coating on the exterior of the transparent substrate, said coating having an exterior which substantially corresponds in shape to that of said transparent substrate, said coating comprising a material which is substantially opaque to said optical energy, said opaque coating being in direct contact with said transparent substrate such that said opaque coating is directly exposed to optical energy, said opaque coating covering the exterior of said transparent substrate throughout substantially the entire tissue contacting portion of said contract tip and forming a reflecting cavity which substantially confines said optical energy within said contact tip, said opaque coating being sufficiently reflective to optical energy at said wavelength such that said confined optical energy undergoes multiple reflections which distribute said optical energy within said cavity to substantially uniformly heat the coating on said tissue contacting portion of said contact tip.

20. The apparatus of claim 5, wherein said coating consists essentially of a single coating material.

21. The apparatus of claim 20, where said single coating material consists essentially of biologically compatible material.

22. The apparatus of claim 21, wherein said coating material comprises at least one biologically compatible metal selected from the group consisting of tantalum, vanadium, titanium and tungsten.

23. The apparatus of claim 5, wherein said substantially transparent substrate comprises a crystalline material.

24. The apparatus of claim 23, wherein said crystalline material comprises $Al_2O_3$.

25. The apparatus of claim 19, wherein said coating comprises gold.

26. The apparatus of claim 19, wherein said waveguide comprises an optical fiber.

27. The apparatus of claim 19, wherein said transparent substrate is substantially conical.

28. The apparatus of claim 27, wherein said coating consists of tantalum.

29. The apparatus of claim 19, wherein said wavelength is infrared.

30. The apparatus of claim 29, wherein said laser comprises a Nd:YAG laser.

31. The apparatus of claim 29, wherein said laser comprises an Er:YAG laser.

* * * * *